US007053054B2

(12) United States Patent
Paradisi et al.

(10) Patent No.: US 7,053,054 B2
(45) Date of Patent: May 30, 2006

(54) PURIFIED LH

(75) Inventors: Gianfranco Paradisi, Monterotondo (IT); Mara Rossi, Rome (IT); Laura Scaglia, Rome (IT)

(73) Assignee: Applied Research Systems ARS Holding N.V., Curacao (AN)

( * ) Notice: Subject to any disclaimer, the term of this patent is extended or adjusted under 35 U.S.C. 154(b) by 472 days.

(21) Appl. No.: 10/204,554

(22) PCT Filed: Jan. 22, 2001

(86) PCT No.: PCT/EP01/00666

§ 371 (c)(1),
(2), (4) Date: Dec. 11, 2002

(87) PCT Pub. No.: WO01/62774

PCT Pub. Date: Aug. 30, 2001

(65) Prior Publication Data

US 2003/0186893 A1  Oct. 2, 2003

(30) Foreign Application Priority Data

Feb. 22, 2000 (EP) ................... 00103692

(51) Int. Cl.
*A61K 38/00* (2006.01)
(52) U.S. Cl. ..................................... 514/16
(58) Field of Classification Search ............ 514/16
See application file for complete search history.

(56) References Cited

FOREIGN PATENT DOCUMENTS

| WO | WO 90/02757 | 3/1990 |
|----|-------------|--------|
| WO | WO 90/09800 | 9/1990 |
| WO | WO 98/20039 | 5/1998 |
| WO | WO 98/58957 | 12/1998 |

OTHER PUBLICATIONS

Camero, et al., Aislamiento Y Purification De Hormona Luteinizante Humana, Revista Colombina Dde Quimica, 1993, vol. 22, No. 1, pp. 69-77 and translation.*
Rivier, Reversed-Phase high performance Liquid Chromatography: Preparative Purification of Synthetic peptides, journal of Chromatography, 1984, vol. 288, pp. 303-328.*
Barnthouse, et al, "Cation-exchange Displacement Chromatography for the Purification of Recombinant Protein Therapeutics from Variants", *J. of Biotechnology*, 66: 125-136, XP002138425 (1998).
DYR, et al, "Separation Used for Purification of Recombinant Proteins", *J. of Chromatography B*. 699: 383-401 XP-002138424 (1997).
Eder, et al, "New cation-exchange Resins with High Reversed-phased Character fro Solid-phase Extraction of Phenols", *J. of Chromatography A*, 810: 43-52 (1998).

* cited by examiner

Primary Examiner—Christopher R. Tate
Assistant Examiner—Jennifer Harle
(74) Attorney, Agent, or Firm—Browdy and Neimark, PLLC

(57) ABSTRACT

A process for the purification of recombinant human Luteinizing Hormone (LH) from a sample of crude recombinant LH in the supernatant of CHO cells comprises the combined use of the ion-exchange chromatography and reverse phase HPLC. The ion-exchange chromatography and the reverse phase HPLC are performed twice and the final use of a gel permeation column allows the purification from any residual traces of contaminants. The specific bioactivity of the highly purified LH obtained from the process is particularly high, amounting to 25,000 IU/mg.

10 Claims, No Drawings

PURIFIED LH

FIELD OF INVENTION

The present invention relates to a process for the purification of Luteinising Hormone (LH), in particular the purification of recombinant LH (r-LH) from a sample of crude recombinant LH, comprising the combined use of ion-exchange chromatography and reverse phase HPLC.

Luteinising Hormone (LH) is a gonadotropin secreted by the anterior lobe of the pituitary together with another gonadotropin, follicle-stimulating hormone (FSH). These hormones are heterodimers consisting of non-covalently bound α and β subunits.

These gonadotropins stimulate the normal functioning of the gonads and the secretion of sex hormones in both men and women. In women, follicle-stimulating hormone stimulates the development and maturation of the follicles and ova. As the follicle develops it produces oestrogen in increasing amounts which at mid-cycle stimulates the release of LH. This causes rupture of the follicle with ovulation and converts the follicle into the corpus luteum which secretes progesterone. In men, luteinising hormone stimulates the interstitial cells of the testis to secrete testosterone, which in turn has a direct effect of the seminiferous tubules. Gonadotrophic substances with luteinising or follicle-stimulating activity or both are used in the treatment of fertility disorders, chiefly in females but also in males. Such substances include chorionic gonadotropin which possesses LH activity and human menopausal gonodotropins which possess both LH and FSH activity. A recombinant DNA-derived human luteinising hormone (rechLH) is being investigated as an alternative to chorionic gonadotropin or for administration in conjunction with FSH.

Various methods have been used to isolate and purify LH, such as ion-exchange, gel-filtration and immunoaffinity chromatography (Jack, G. W., Blazek, R., James, K., Boyd, J. E. & Micklem, L. R. The automated production by immunoaffinity chromatography of the human pituitary glycoprotein hormones thyrotropin, follitropin and lutropin. Journal of Chemical Technology and Biotechnology 39, 45–58, 1987). Ion-exchange chromatography has been used for the isolation of these hormones, however, this method appears to have several interrelated problems caused by the considerable charge heterogeneity of LH in pituitary tissue. First, because these glycoproteins and FSH have overlapping charges, their complete separation is difficult and laborious. Secondly, the purification of these hormones as single fractions may be difficult (Stockell Hartree, A., Thomas, M., Furnival, B. E., Burns, T. W. & Langley, P. Thyroid-stimulating and lipolytic activities of purified preparation s of human thyroid-stimulating hormone. Journal of Endocrinology 53, 95–100, 1972). As a result, certain. charged forms of the hormone may be selected during purification as suggested in the case of LH (Storring, P. L. Zaidi, A. A., Mistry, Y. G. Lindberg, M., Stenning, B. E. & Diczfalusy, E. A comparison of preparations of highly purified human pituitary luteinising hormone: differences in the luteinising hormone potencies as determined by in vivo bioassays, in vitro bioassay and immunoassay. Acta Endocrinologica 101, 339–347, 1982). Selective purification will further complicate the characterization of these heterogeneous forms, including the structural analysis of their carbohydrate components. Variation in the content of anionic oligosaccharides that contain sialyl and sulphate groups may be the major cause of charge heterogeneity in LH.

Conventional fractionation methods have been described for the preparation of human urinary luteinising hormone (LH) with a potency of 982 i.u. /mg by biological assay and 1166 i.u. by radioimmunoassay (Donini S. & Donini P. Acta endocr., Copenh. 63, Suppl. 142, 257–277, 1969). An immunoabsorbent of rabbit antiserum to purified human chorionic gonadotropin (HCG) was used to purify LH from the main and side fractions obtained during the preparation of follicle-stimulating hormone (FSH) from menopausal urine (van Hell, H., Schuurs A. H. W. M. & den Hollander, F. C. In Symposium on gonadotrophins, New York, 17 Jun. 1971. Eds B. B. Saxena, C. G. Beling & H. M. Gandy. New York: John Wiley & Son, Inc, 1972). The preparation obtained had higher LH potencies, but also higher FSH:LH ratios than those prepared by Donini & Donini (1969).

Recombinant LH has the advantage of being devoid of other gonadotropin hormones, such as FSH and TSH. The crude preparation of recombinant LH contains, however, all other proteins and contaminants of the cell used in its recombinant production and a method for achieving an absolute purity of recombinant Luteinising hormone is highly desirable.

SUMMARY OF THE INVENTION

We have now found that a crude preparation of LH, derived from a sample of the culture medium obtained after the recombinant process or from a crude concentrate of post-menopausal urine can be purified to such a degree that the resulting LH is practically free from proteins and/or other contaminants contained in the crude LH preparation. Depending on the starting material, the protein and other contaminants are from human origin (starting material: human menopausal gonadotropins) or from host cell origin, e.g. CHO in case of a CHO host cell.

The purification process is based on the use of ion-exchange chromatography and reverse phase HPLC. The optional further use of a gel permeation column allows the removal of any residual traces of contaminants from the pure LH preparation. Optimum results are obtained when two steps of ion-exchange chromatography and two steps of reverse phase HPLC are performed.

The process of the invention can be used for the purification of recombinant LH, starting from a sample of a culture medium obtained after the recombinant process, such that the resulting highly purified LH is practically free, for example, from FBS proteins often contained in the culture medium, nucleic acids or other contaminants present in the host cells used for the recombinant process The process of the invention can be used as well for the purification of urinary LH, starting from a crude concentrate of post-menopausal urine, and for the purification of LH from other species, particularly mammalian, including, for example, bovine, equine, porcine, ovine, rat, mouse and monkey.

It is, therefore, an object of the present invention to provide a process for purification of LH from a sample comprising the combined use of ion-exchange chromatography and reverse phase HPLC. The process comprises the steps of subjecting the sample (if necessary concentrated) to ion-exchange chromatography and subjecting the eluate to reverse phase HPLC. A further step of applying the eluate to a gel permeation column may additionally be carried out.

Depending on the purity of the starting preparation, the ion-exchange chromatography and the reverse phase HPLC are preferably performed twice in order to obtain optimum results from the purification process. Such a process may comprise the steps of:
- (a) eluting the sample through a DEAE Sepharose ion-exchange chromatography column;
- (b) eluting through a Q-Sepharose ion-exchange chromatography column;
- (c) eluting through a Silica C18 reverse phase HPLC column;
- (d) again eluting through a Silica C18 reverse phase HPLC column [optionally with a different eluent from step (c)]; and
- (e) eluting through a gel permeation column.

In a preferred embodiment of the invention, elution through the DEAE Sepharose ion-exchange chromatography is carried out in sodium phosphate buffer at pH 8.

Elution through the Q-Sepharose ion-exchange chromatography is preferably carried out in ammonium acetate buffer at pH 7.5.

The reverse phase HPLC step (c) is preferably carried out with 2-propanol/ammonium acetate as mobile phase.

The reverse phase HPLC step (d) is preferably carried out with 2-propanol/Tris-HCl as mobile phase.

The LH of the present invention is preferably human LH and most preferably is recombinant human LH, deriving from the culture medium of mammalian cells (preferably CHO cells) used in the recombinant process.

It is a further object of the present invention to provide a pharmaceutical composition comprising a therapeutically effective amount of the recombinant LH as prepared by the recombinant process as described above, together with suitable excipients, such as sucrose, necessary for the stabilisation of the lyophilised product. The pharmaceutical composition of the recombinant LH is particularity suitable for subcutaneous administration.

DETAILED DESCRIPTION OF THE INVENTION

The invention provides a method for the purification of LH, in particular for the purification of recombinant LH from a crude preparation in the culture medium of the recombinant process. r-hLH is obtained with a high degree of purity and high specific activity, practically free from Foetal Bovine Serum (FBS) proteins if present in the culture medium and from nucleic acids or other contaminants contained in the host cells used in the recombinant process.

The invention is intended for use with biological materials, particularly crude mixtures containing LH and other contaminating proteins referred to herein as starting material samples. The examples described in detail below use starting material samples containing r-hLH, obtained from culture supernatant medium from a bioreactor. Alternatively, the sample is human Menopausal Gonadotropin (hMG), a crude concentrate of post-menopausal urine.

The sample is constituted by freshly collecting cell culture supernatant medium perfused through a bioreactor. It is preferably clarified by filtration. The crude solution can then be concentrated, if necessary, and subjected to ultrafiltration to remove material having molecular weights lower than 10. Ultrafiltration also permits the buffer to be changed to sodium phosphate, pH 8.

After the preliminary steps, the sample is then subjected to ion-exchange chromatography and to reverse phase HPLC, which are preferably each performed twice. The first ion-exchange step is preferably carried out with DEAE Sepharose. This is essentially an LH "flow-through" step in which a large part of the non-LH proteins are eliminated. The second ion-exchange step is preferably carried out with a Q-Sepharose column. This is also an LH "flow through" step and is designed to remove potential DNA and host cell or medium protein contaminants. In a preferred embodiment this step is performed at about 5° C. eluting with ammonium acetate buffer at pH 7.5.

Reverse phase chromatography on Silica C18 is also preferably performed twice and is effective in removing trace amounts of FBS, cell protein and endotoxin contaminants. The first HPLC step is preferably carried out with 2-propanol/ammonium acetate as mobile phase. The second reverse phase HPLC step is preferably performed using 2-propanol/Tris-HCl as mobile phase. The retentate solution is then concentrated and can be recovered with ammonium hydrogen carbonate, pH 8. The concentrated product is preferably subjected to Gel permeation chromatography on Sephacryl S100 HR. In this step, a separation based on molecular size is achieved eluting with ammonium hydrogen carbonate pH 8 and the eluate then undergoes preferably a filtration to remove viral contaminants, then an ultrafiltration on membranes with 10 KD cut-off in sodium phosphate buffer, pH 8. After filtration, the purified LH bulk is preferably stored in sterile bottles at low temperature.

EXAMPLE 1

Reagents

Acetic acid (glacial), analytical grade (Ph.Eur.)
Ammonium acetate, analytical grade
Ammonium hydrogen carbonate, analytical grade (B.P.)
Dibasic sodium phosphate, analytical grade
Hydrochloric acid, analytical grade (Ph.Eur.)
Phosphoric acid, analytical grade (Ph.Eur.)
2-propanol, analytical grade (Ph.Eur.)
Sodium chloride, analytical grade (Ph.Eur.)
Monobasic sodium phosphate, analytical grade
Sodium hydroxide pellets, analytical grade (Ph.Eur.)
Trifluoroacetic acid (TFA), HPLC grade
Tris-(hydroxymethyl) aminomethane, analytical grade
Water for Injection (WFI)(Ph.Eur.)

Purification Process Summary Flow Diagram

Table 1 is a flow diagram summarising the r-hLH purification process, outlining the principles of operation of each of the intermediate steps.

TABLE 1

Flow diagram summarising the r-hLH purification process

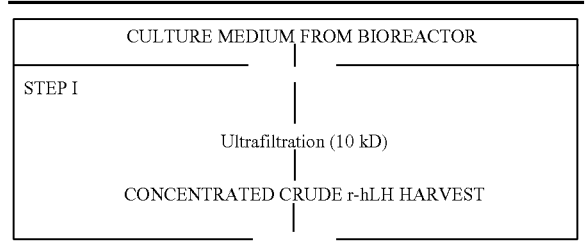

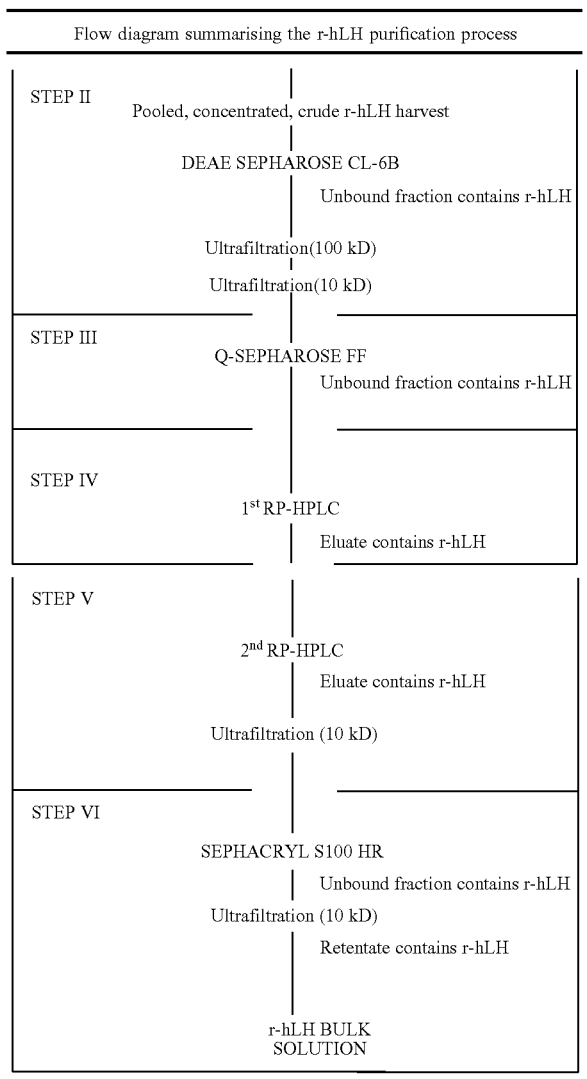

TABLE 1-continued

Flow diagram summarising the r-hLH purification process

Clarification, Concentration, Dialysis and Filtration of Harvests (Step I)

In this step (Step I) the buffer is changed to be of controlled composition and a preliminary concentration is achieved. This step, is carried out at about +5° C. and is repeated individually for each harvest during the production cycle of the bioreactor. A preferred range of temperature is 5±3° C.

(i) Clarification of harvests

Upon receipt of freshly collected culture medium from a bioreactor the material is preferably processed starting with clarification of the supernatant solution by filtration.

(ii) Concentration/dialysis of harvests

The membranes, stored in 0.05M sodium hydroxide between batches, are rinsed with WFI until the pH descends to approximately 8.

The equilibration buffer, 0.025M sodium phosphate pH 8, replaces the water. Once conditioned the crude r-hLH solution from the bioreactor is concentrated and dialysed to remove material having molecular weights lower than 10 kD (membrane cut-off 10 kD).

The resulting concentrate is stored at about −15° C.

Ion Exchange Chromatography on DEAE Sepharose CL-6B (Step II)

The chromatography step is an r-hLH "flow-through" step in which a large part of the non r-hLH proteins are eliminated and the solution is further concentrated and dialysed. The chromatography stages where product passes through the column, is carried out in a cold room.

(i) Ion exchange chromatography on DEAE Sepharose CL-6B

The column is packed with a weakly charged anion-exchange resin, diethyl amino ethane (DEAE) Sepharose, equilibrated in the first instance with 0.15M sodium phosphate pH 8. A preferred pH range is 8±0.3.

The column is then conditioned with the running buffer, 0.025M sodium phosphate pH 8. A preferred pH range is 8±0.3.

The r-hLH solution is loaded onto the column through a filter apparatus, which is located on the column as a guard.

The column is fed with 0.025M sodium phosphate pH 8. A preferred pH range is 8±0.3. The chromatographic process is monitored by spectrophotometry at 280 nm. The leading effluent is discarded until the baseline passes the 5% absorbance mark. The unbound fraction containing the r-hLH is collected until the baseline has descended to 10%.

(ii) Ultrafiltration

An ultrafiltration apparatus, equipped with a 100 kD cut-off membrane, stored in NaOH 0.05M is rinsed with WFI until the pH of the permeate is approximately 8.

The water is replaced by the equilibration buffer 0.08M ammonium acetate pH 7.5. A preferred pH range is 7.5±0.3.

The r-hLH solution obtained from the ion exchange chromatography step is ultrafiltered through the 100 kD membrane and the permeate fraction is collected.

The ultrafilter is washed with aliquots of 0.08M ammonium acetate pH 7.5 and all of the washing fractions are collected into the permeate solution.

(iii) Concentration/dialysis

An ultrafiltration device equipped with a 10 kD cut-off membrane, stored in 0.05M NaOH, is rinsed with WFI until the pH of the permeate fraction is approximately 8. The water is replaced by the equilibration buffer, 0.08M ammonium acetate pH7.5.

The r-hLH solution is concentrated. Ammonium acetate 0.08M pH 7.5 is added to the retentate and the solution concentrated. The dialysis is continued until the pH and conductivity of the retentate are the same as those of the incoming buffer. The resulting retentate is recovered.

Ion Exchange Chromatography on Q Sepharose Fast Flow (Step III)

This step, is also an r-hLH "flow-through" step and is designed to remove potential DNA and host cell or medium protein contaminants.

(i) Column equilibration

Conditioning of the column is performed with running buffer, 0.08M ammonium acetate buffer, pH 7.5. A preferred pH range is 7.5±0.3.

(ii) r-hLH purification step on Q-Sepharose FF

The r-hLH solution is loaded through a filter apparatus which is located on the Q Sepharose column as a guard.

The column is further washed with 0.08M ammonium acetate pH 7.5.

The leading effluent is discarded until the baseline passes the 5% absorbance mark.

The unbound fraction containing the r-hLH is collected until the baseline has descended to 10%.

The r-hLH solution from Step III can be stored frozen for subsequent use. If stored at a temperature of −15° C. or below, the r-hLH intermediate is thawed at +5±3° C., typically over a period of 24±8 hours before undertaking the reverse phase HPLC (Step IV).

First Preparative Reverse Phase HPLC (Step IV)

This step, performed at room temperature, is effective in removing trace amounts of FBS/CHO protein and endotoxin contaminants.

(i) Column packing and resin activation

The column is packed with C18 wide-pore silica and, if new, the C18 resin is conditioned with 2-propanol.

(ii) Column equilibration

The column is equilibrated with 12.4% w/w 2-propanol in 0.05M ammonium acetate buffer, pH 7. A preferred pH range is 7±0.2.

(iii) pH and volume adjustments of r-hLH solution from step III

The r-hLH solution is adjusted to pH 7 with concentrated acetic acid. A preferred pH range is 7±0.2.

The volume of the r-hLH solution is then adjusted by the addition of 2-propanol in order to obtain a final concentration of 2-propanol equal to 12.4% w/w.

(iv) Filtration of adjusted r-hLH solution

The filtration apparatus equipped with a 0.22 µm filter is washed with 12.4% w/w 2-propanol in 0.05M ammonium acetate buffer, pH 7. A preferred pH range is 7±0.2.

The adjusted r-hLH solution is filtered.

The recipient is rinsed with aliquots of 12.4% w/w 2-propanol in 0.05M ammonium acetate buffer, pH 7, filtered and the rinses pooled with the r-hLH solution. A preferred pH range is 7±0.2.

(v) r-hLH purification step on the first C18 RP-HPLC column

The r-hLH solution is loaded onto the column and the chromatography is monitored by UV spectrophotometry at 280 nm.

The column is fed with 12.4% w/w 2-propanol in 0.05M ammonium acetate buffer, pH 7 until the $A_{280}$ returns to baseline whereupon the unbound fraction is discarded.

Elution of the r-hLH is subsequently performed with a 2-propanol/ammonium acetate 0.05 M mobile phase across a linear gradient from 14.7% to 20.7% w/w 2-propanol.

The r-hLH is fractioned when the $A_{280}$ starts to increase. All fractions of the r-hLH peak whose heights are greater than 20% of full scale are pooled.

Second Preparative Reverse Phase HPLC Column (Step V)

This step, performed at room temperature, is effective in removing trace amounts of FBS/CHO protein and endotoxin contaminants.

(i) Column packing and resin activation

The column is packed with C18 wide-pore silica and, if new, the C18 resin is conditioned with 2-propanol.

(ii) Column equilibration

The column is equilibrated in 14.7% w/w 2-propanol in 0.5M Tris-HCl buffer, pH 7.

A preferred pH range is 7±0.2.

(iii) Volume and pH adjustments of r-hLH solution from Step IV

2M Tris-HCl buffer, pH 7 is added to the r-hLH sample in order to bring the 2-propanol concentration down to approximately the same as that in the column equilibration buffer (14.7% w/w).

The r-hLH solution is adjusted to pH 7 with HCl 12M. A preferred pH range is 7±0.2.

(iv) r-hLH purification step on the second C18 RP-HPLC column

The r-hLH solution is loaded onto the column and the chromatography is monitored by UV spectrophotometry at 280 nm.

The column is fed with 14.7% w/w 2-propanol in 0.5M Tris-HCl buffer, pH 7. A preferred pH range is 7±0.2. The unbound fraction is discarded.

Elution of the r-hLH is subsequently performed with a 2-propanol/0.5M Tris-HCl mobile phase across a linear gradient from 14.7% to 20.7% w/w 2-propanol.

The r-hLH is fractioned when the $A_{280}$ starts to increase. All fractions of the r-hLH peak whose heights are greater than 20% of full scale are pooled.

(v) Dialysis

The r-hLH solution from the second C18 RP-HPLC step is diluted with WFI.

Preferably 8 volumes of WFI are used.

The diluted r-hLH solution is dialysed by ultrafiltration on a 10 kD membrane (see page 7, step VI) against WFI. Aliquots of 0.5M ammonium hydrogen carbonate pH 8 are subsequently added and the dialysis continued until the characteristics of the ammonium hydrogen carbonate buffer are met.

The retentate solution is concentrated to a final volume of approximately 1L and recovered. The ultrafilter is washed with 0.5M ammonium hydrogen carbonate pH 8 and the ultrafiltration washes are pooled with the retentate and optionally further concentrated. This further concentration is dependent on the size of the column used in the next step, i.e. Step VI.

Gel Permeation Chromatography on Sephacryl S100 HR and Ultrafiltration (Step VI)

In this step, a separation based on molecular size is achieved and the solution undergoes ultrafiltration. All operations performed in this step are carried out at about +5° C. A preferred temperature range is +5° C.±3.

(i) Gel permeation chromatography on Sephacryl S100 HR

The column is packed with Sephacryl S100 HR and is equilibrated in the first instance with WFI.

The column is then equilibrated with 0.5M ammonium hydrogen carbonate pH 8.

The column is fed with 0.5M ammonium hydrogen carbonate pH 8. The chromatographic process is monitored by spectrophotometry at 280 nm.

The r-hLH is fractioned when the $A_{280}$ starts to increase. All fractions of the r-hLH peak whose heights are greater than 20% of full scale are pooled.

The r-hLH solution, eluted from the Sephacryl S100 HR column, is then preferably passed through a filter, e.g. Virosolve™, to remove viral contaminants.

(ii) Dialysis and concentration of r-hLH

The membranes (ultrafiltration membranes 10 kD), stored in 0.05M sodium hydroxide between purification runs, are rinsed with WFI until the pH descends to approximately 8.

The diluted r-hLH solution is dialysed (by ultrafiltration membranes 10 kD) against WFI. Aliquots of 0.01M sodium phosphate buffer, pH 8 are subsequently added and the dialysis continued until the characteristics of the sodium phosphate buffer are met.

If necessary the retentate solution is concentrated to a final volume of approximately 500 ml and recovered. The ultrafilter is washed with 0.01M sodium phosphate buffer, pH 8 and the ultrafilter washes are pooled with the retentate.

A further optional LH concentration step can be performed depending on the condition selected for storage.

The r-hLH solution is filtered and the filtrate collected into a sterile vessel.

The purified r-hLH bulk is preferably stored in sterile bottles at about −15° C.

Reagents, Buffers, Eluants and Chemicals

Chromatographic Resins

The following chromatographic resins are currently employed in the purification process. Equivalent resins can be employed as well in the purification process.

| Step II:  | DEAE Sepharose CL-6B | (Pharmacia) |
| Step III: | Q-Sepharose Fast Flow | (Pharmacia) |
| Step IV:  | C18 Silica RP-HPLC   | (Waters)    |
| Step V:   | C18 Silica RP-HPLC   | (Waters)    |
| Step VI:  | Sephacryl S100 HR    | (Pharmacia) |

The suppliers are:
Amersham Pharmacia Biotech, Björkgatan 30 S-751 84, Uppsala Sweden
Waters Corporation 34 Maple Street Milford, MA 01757 USA Results Biological Activity Biological Activity of different batches of r-LH after purification with the method of the present invention is reported in Table 2. The protein concentration (mg of LH protein/ml) has been determined by spectrophotometry at 276.5 nm, using the experimentally derived absorptivity based on amino acid sequence analysis a=0,812

The average specific activity of the r-LH preparation is particularly high, amounting to about 25.000 IU/mg (of protein of LH).

TABLE 2

Specific activity of r-hLH bulk batches

| N° lot | Spec act [IU/mg] |
| --- | --- |
| BLCA 9802 | 28173 |
| BLCA 9803 | 25819 |
| BLCA 9804 | 27472 |
| BLCA 9805 | 31229 |
| BLCA 9806 | 26995 |
| BLCA 9808 | 26279 |
| BLCA 9809 | 20522 |
| BLCA 9810 | 22275 |
| BLCA 9811 | 27642 |
| BLCA 9812 | 29941 |
| BLCA 9813 | 28345 |
| BLCA 9814 | 27581 |
| BLCA 9815 | 24541 |

Formulations

Freeze dried formulations have been developed with highly purified recombinant LH of the present invention.

As a typical example, a freeze dried formulation at 75 IU strength was prepared in vials DIN 2R using sucrose as excipient (Table 3), which resulted stable at 4° C. for several months.

TABLE 3

| Name of ingredients | Unit formula |
| --- | --- |
| Active ingredient | |
| Recombinant human LH | 3.4 mcg (75 IU) |
| Other ingredient | |
| Sucrose | 47.75 mg |
| Tween 20 | 0.05 mg |
| Disodium phosphate dihydrate | 0.825 mg |
| Monosodium phosphate monohydrate | 0.052 mg |

What is claimed is:

1. A process for purification of recombinant LH from a sample, comprising:
   subjecting said sample to ion-exchange chromatography with an anion exchange resin;
   subjecting said sample to reverse phase HPLC; and
   isolating the recombinant LH.

2. A process according to claim 1, comprising the steps of:
   (a) subjecting the sample to ion-exchange chromatography to produce a first eluate;
   (b) subjecting the first eluate to reverse phase HPLC, to produce a second eluate;
   (c) subjecting the second eluate to gel permeation chromatography; and
   (d) isolating the recombinant LH.

3. A process according to claim 1, wherein the ion-exchange chromatography and the reverse phase HPLC are performed twice.

4. A process according to claim 1, comprising the steps of:
   (a) eluting the sample through a DEAE Sepharose ion-exchange chromatography column;
   (b) eluting through a Q-sepharose ion-exchange chromatography column;
   (c) eluting through a Silica C18 reverse phase HPLC column;
   (d) further eluting through a Silica C18 reverse phase HPLC column;
   (e) eluting through a gel permeation column; and
   (f) isolating the recombinant LH.

5. A process according to claim 4, wherein elution through DEAE Sepharose ion-exchange chromatography is carried out in sodium phosphate buffer at about pH 8.

6. A process according to claim 4, wherein elution through Q-Sepharose ion-exchange chromatography is carried out in ammonium acetate buffer at about pH 7.5.

7. A process according to claim 4, wherein the reverse phase HPLC step (c) is carried out with 2-propanol/ammonium acetate as mobile phase.

8. A process according to claim 4, wherein the reverse phase HPLC step (d) is carried out with 2-propanol/Tris-HCl as mobile phase.

9. A process according to claim 1, wherein the recombinant LH is human LH.

10. A process according to claim 1, wherein the sample is a culture medium from CHO cells.

* * * * *